US00PP17359P2

(12) United States Plant Patent
Olesen

(10) Patent No.: US PP17,359 P2
(45) Date of Patent: Jan. 16, 2007

(54) MINIATURE ROSE PLANT NAMED 'POULPAH035'

(50) Latin Name: ***Rosa* hybrid**
Varietal Denomination: Poulpah035

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 10 days.

(21) Appl. No.: 11/266,616

(22) Filed: Nov. 4, 2005

(51) Int. Cl.
*A01H 5/00* (2006.01)

(52) U.S. Cl. ..... Plt./122

(58) Field of Classification Search ..... Plt./122
See application file for complete search history.

*Primary Examiner*—Kent Bell
*Assistant Examiner*—June Hwu

(57) ABSTRACT

A new miniature rose plant that has abundant, dark red flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulpah035'.

SUMMARY OF THE INVENTION

The present invention constitutes a new and distinct variety of miniature rose plant which originated from a controlled crossing between the female seed parent, an unnamed seedling, and the male pollen parent an-unnamed seedling.

The two parents were crossed during the summer of 2002 and the resulting seeds were planted in a controlled environment in Fredensborg, Denmark. The new variety, named 'Poulpah035', originated as a single seedling from the stated cross.

The new variety may be distinguished from its female seed parent by the following combination of characteristics:

1. The seed parent is less compact in growth habit than 'Poulpah035'.

The new variety may be distinguished from its male pollen parent by the following combination of characteristics:

1. Flowers of the pollen parent have more than 50 flower petals, while flowers of 'Poulpah035' have 40 to 50 flower petals.
2. Flowers of 'Poulpah035' are red, while flowers of the pollen parent are red to red-purple.

The objective of the hybridization of this rose variety for commercial culture was to create a new and distinct variety with unique qualities, such as:

1. Uniform and abundant dark red flowers which retain their color as flowers mature;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventors, and distinguish 'Poulpah035' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpah035' was selected by the inventor as a single plant from the progeny of the hybridization in April 2003.

Asexual reproduction of 'Poulpah035' by cuttings and traditional budding was first done by Mogens N. Olesen in the nursery in Fredensborg, Denmark in 2003. This initial and other subsequent propagations conducted in controlled environments have demonstrated that the characteristics of 'Poulpah035' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpah035'. Specifically illustrated in the drawing:

FIG. 1.1; Flower bud closed, partially open, and fully open flower;

FIG. 1.2; Receptacle, sepals, and exposed reproductive flower parts;

FIG. 1.3; Flower petals, detached;

FIG. 1.4; Bare stem;

FIG. 1.5; Mature leaves;

FIG. 1.6; Juvenile leaves.

DETAILED DESCRIPTION OF THE VARIETY

The following is a description of 'Poulpah035', as observed in its growth in glasshouses in Fredensborg, Denmark. Observed plants are 4 months of age and were cultivated in 12 cm pots. Color references are made using The Royal Horticultural Society (London, England) Colour Chart, 2001, except where common terms of color are used.

For a comparison, several physical characteristics of the rose variety 'Poulhi021', U.S. Plant Pat. No. 15,853 issued on Jul. 12, 2005, are compared to 'Poulpah035' in Chart 1.

CHART 1

| | 'Poulpah035' | 'Poulhi021' |
|---|---|---|
| Color of filaments: | Basal portion is Greyed-Yellow 162D. Upper portion is Red-Purple 63B. | Yellow-Green 150D. |
| Flower Diameter: | 100 to 110 mm | 50 to 55 mm. |
| General Tonality of Flower Color: | Red 53B with intonations of Red-Purple 60A and Red-Purple N57A. | Red 42A to Red 53B. |

FLOWER AND FLOWER BUD

Blooming habit: Continuous.

Flower bud:

*Size.*—Upon opening, 30 to 35 mm in length from base of receptacle to end of bud. 12 to 14 mm in diameter.

*Bud form.*—Ovate.

*Bud color.*—As sepals unfold, petals are Red Group 53A with occasional streaks or splotches of Yellow-Green Group 145B.

*Sepals.*—Upper Surface: Color: Green Group 138B. The apecies are occasionally colored Yellow-Green Group 146A. Surface: Medium amount of pubescence. Lower Surface: Color: Yellow-Green Group 144B. Texture: Smooth with few stipitate glands and light pubescence. Shape: Apex: Cirrhose. Base: Flat at union with receptacle. Margins: Margins have medium to weak foliaceous appendages on three of the five sepals. Size: 30 mm long by 10 mm wide.

*Receptacle.*—Surface Texture: Smooth. Shape: Urn-shaped. Size: 9 mm (h)×11 mm (w). Color: Yellow-Green Group 144A. Anthocyanin: None observed.

*Pedicel.*—Surface: Smooth with stipitate glands. Length: 25 mm average length. Diameter: 3 mm. Color: Yellow-Green Group 144A. Strength: Medium strength. Scent: Stipitate glands release strong pine scent when touched.

*Borne.*—Singularly and occasionally in clusters of 3 flower buds per stem.

Flower bloom:

*Fragrance.*—None.

*Duration.*—As a pot plant, flowers last from up to 28 days. Petals do not fall cleanly away from plant.

*Size.*—Fully open diameter is 100–110 mm. Depth is 35 to 40 mm.

*Form.*—Double with a high pointed center which is tightly closed.

*Shape of flower, side view.*—Upon opening, the upper portion is flattened convex. The lower portion is flat. After opening, the upper portion is flatted convex. The lower portion is flat.

*Petalage.*—There are normally 45 to 50 petals under normal conditions, 15 of which are petaloids.

*Flower color.*—Upon opening, petals: Outermost petals: Upper Surface: Red Group 46A to 53 A with occasional streaks the color of White Group N155B. Lower Surface: Red-Purple Group 60A to Red Group 53C. Innermost petals: Upper Surface: Red Group 46A to 53A Lower Surface: Red-Purple Group 60A to Red Group 53C. Upon opening, basal petal spots: Upper Surface: White Group N155B. Lower Surface: White Group N155B. After opening, petals: Outermost and innermost petals: Upper Surface: Red Group 53A with light intonations of Red-Purple Group N57A at marginal zone. Lower Surface: Red-Purple Group 60A to 60B. After opening, basal petal spots: Upper Surface: White Group N155B. Lower Surface: White Group N155B.

General tonality: On open flower Red Group 53B with intonations of Red-Purple Group N57A. After peak maturity flowers become Red Group 53B to 53C with intonations of Red-Purple Group N57A.

Petals:

*Petal reflex.*—Slightyly reflexed.

*Petal margin.*—Entire with slight point at the center. Weak undulations of margin observed.

*Shape.*—Broad elliptical. Base: Acute. Apex: Rounded.

*Size.*—Petal size varies. Outer petals: 45 mm (l)×45 mm (w). Inner petals: 35 mm (l)×35 mm (w).

*Thickness.*—Above average.

*Texture.*—Smooth. Lower surfaces of petals occasionally exhibit lines of light pubescence.

Petaloids:

*Size.*—Generally 15 mm long; 10 mm wide.

*Shape.*—Irregular.

*Color.*—Upper Surface: Red Group 46A to 53 A with occasional streaking of White Group N155B to Yellow-Green Group 144D. Lower Surface: Red-Purple Group 60A to Red Group 53C.

Reproductive organs:

*Pollen.*—None observed.

*Anthers.*—Size: 3 to 4 mm long. Color: Orange-White Group 159C. Quantity: 115 to 120.

*Filaments.*—Color: Base: Greyed-Orange Group 162D. Upper: Red-Purple Group 63B. Length: Approximately 10 mm.

*Pistils.*—Length: Approximately 10 mm long. Quantity: 100 to 110.

*Stigmas.*—Inferior relative to the length of the filaments and the height of the anthers. Color: Greyed-Yellow Group 160B.

*Styles.*—Color: Red-Purple Group 61B.

*Seed formation.*—Not observed.

PLANT

Plant growth: Upright and bushy. When grown as a 12 cm pot plant on its own roots, the average height of the plant itself is 20 to 25 cm and the average width is 20 cm.

Stems:

*Color.*—Young wood: Yellow-Green Group 146B. Older wood: Yellow-Green Group 146A with Greyed-Purple 184A.

*Internodal distance.*—35 mm.

*Length of stems.*—18 to 20 cm from the base of the stem to the flowering portion.

*Diameter.*—4 mm.

*Surface texture.*—Young wood: Smooth. Older wood: Smooth with thorns.

Thorns:

*Incidence.*—10 to 12 thorns per 10 cm of stem.

*Size.*—Normally 2 to 5 mm.

*Color.*—Juvenile thorns are Greyed-Purple Group 182A. Mature thorns are Greyed-Purple Group 182A.

*Shape.*—Upper side: Flat. Lower side: Flat.

Plant foliage: Normal number of leaflets on normal leaves in middle of the stem: 5 to 7 leaflets.

*Compound leaf size.*—90 to 100 mm (l)×65 to 75 mm (w).

*Quantity.*—4 leaves per 10 cm of stem.

*Color.*—Juvenile foliage: Upper Leaf Surface: Yellow-Green Group 146A. Lower Leaf Surface: Yellow-Green Group 147C. Mature foliage: Upper Leaf Surface: Yellow-Green Group 147A. Lower Leaf Surface: Yellow-Green Group 148C.

Plant leaves and leaflets:

*Stipules.*—Size: 8 mm in length. Shape: Linear, slightly broad based with outward extending apecies. Margins: Finely serrated with many stipitate glands. Color: Yellow-Green Group 146A.

*Petiole.*—Length: 20 mm in length. Diameter: 1.5 mm. Upper Surface: Color: Yellow-Green Group 146A. Anthocyanin: Greyed-Purple Group 187A. Underneath: Few stipitate glands observed. Lower Surface: Color: Yellow-Green Group 146B. Underneath: Few small prickles observed.

*Rachis.*—Size: 25 to 30 mm in length. Upper Surface: Color: Yellow-Green Group 146A. Anthocyanin: Greyed-Purple Group 187A. Observations: Few stipitate glands. Lower Surface Color: Yellow-Green Group 146B. Observations: Few small prickles.

*Leaflet.*—Size: 40 to 50 mm in length by 30 to 35 mm wide. General Shape: Ovate. Apex Shape: Acute. Base Shape: Rounded. Texture: Smooth. Thickness: Average. Arrangement: Odd pinnate. Venation: Reticulate. Leaf Gloss: Slightly glossy finish.

Disease resistance: Average resistance to powdery and downy mildew, black spot, and *Botrytis* under normal growing conditions in Fredensborg, Denmark.

What is claimed is:

1. A new and distinct variety of rose plant of the miniature class named 'Poulpah035', substantially as illustrated and described herein, due to its abundant, dark red flowers, vigorous growth, compact habit, suitability for production from softwood cuttings in pots, and durable flowers and foliage that make the variety suitable for distribution in the floral industry.

* * * * *

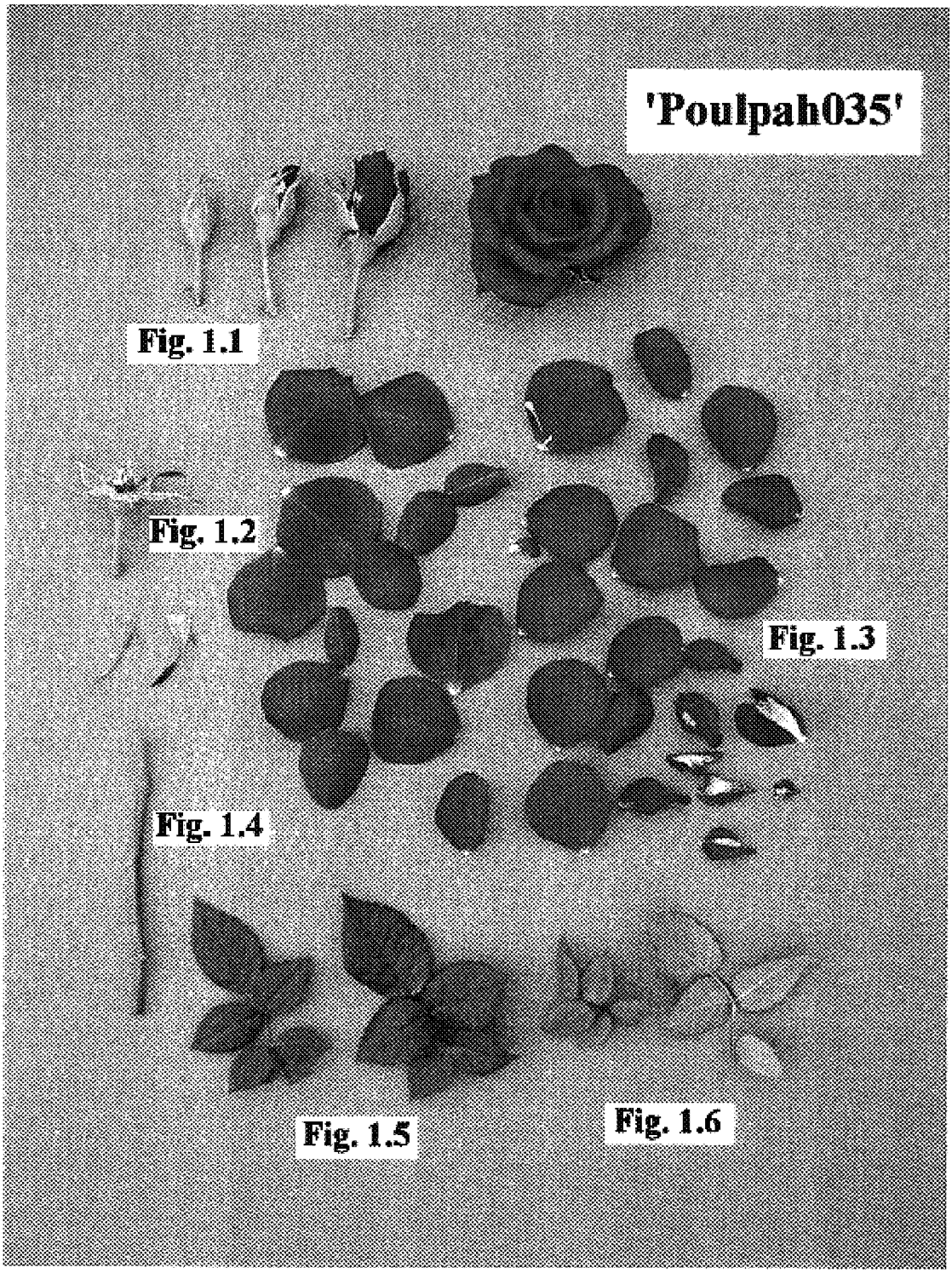
'Poulpah035'
Fig. 1.1
Fig. 1.2
Fig. 1.3
Fig. 1.4
Fig. 1.5
Fig. 1.6